(12) United States Patent
Qasem et al.

(10) Patent No.: US 12,029,538 B2
(45) Date of Patent: Jul. 9, 2024

(54) WEARABLE DEVICE WITH PLETHYSMOGRAM SENSOR

(71) Applicant: AtCor Medical Pty Ltd, Sydney (AU)

(72) Inventors: Ahmad M. Qasem, Guildford (AU); Lawrence Chan, South Hurstville (AU)

(73) Assignee: ATCOR MEDICAL PTY LTD, Sydney (AU)

(*) Notice: Subject to any disclaimer, the term of this patent is extended or adjusted under 35 U.S.C. 154(b) by 482 days.

(21) Appl. No.: 17/331,873

(22) Filed: May 27, 2021

(65) Prior Publication Data

US 2021/0369129 A1   Dec. 2, 2021

Related U.S. Application Data

(60) Provisional application No. 63/031,645, filed on May 29, 2020.

(51) Int. Cl.
*A61B 5/024* (2006.01)
*A61B 5/00* (2006.01)
*A61B 5/021* (2006.01)

(52) U.S. Cl.
CPC ........ *A61B 5/02438* (2013.01); *A61B 5/0022* (2013.01); *A61B 5/02116* (2013.01);
(Continued)

(58) Field of Classification Search
CPC ............ A61B 5/02416; A61B 5/02108; A61B 5/7253; A61B 5/02116; A61B 5/7278; A61B 5/02427
See application file for complete search history.

(56) References Cited

U.S. PATENT DOCUMENTS 5,265,011 A * 11/1993 O'Rourke ............ A61B 5/7239
128/920
6,334,065 B1 * 12/2001 Al-Ali ................... A61B 5/0205
600/323

(Continued)

FOREIGN PATENT DOCUMENTS

| EP | 1380254 | 1/2004 | |
|---|---|---|---|
| WO | 2016040253 | 3/2016 | |
| WO | WO-2021240439 A1 * | 12/2021 | ........... A61B 5/0022 |

OTHER PUBLICATIONS

Lazazzera et al., "A New Wearable Device for Blood Pressure Estimation Using Phtoplethysmogram", Sensors 2019, 19, 2557, 18 pages.

(Continued)

*Primary Examiner* — Oommen Jacob
(74) *Attorney, Agent, or Firm* — Andrus Intellectual Property Law, LLP

(57) ABSTRACT

Central blood pressure parameters are monitored using a smart watch or smart band. A PPG sensor on the smart watch or smart band is adapted to sense blood perfusion in the finger (or lower wrist/radial artery) of the person wearing the smart watch or smart band. The PPG signal captures cardiovascular features which can be detected after proper filtering and processing. Signal processing, using the transfer function method, results in an un-calibrated central pressure waveform, which can be used to calculate various cardiovascular parameters or indicators of the parameters that are displayed on the smart watch or smart band. Digital signal processing can be implemented on the smart watch or smart band, on a smart phone, laptop or in the Cloud.

20 Claims, 15 Drawing Sheets

(52) U.S. Cl.
CPC .......... *A61B 5/02427* (2013.01); *A61B 5/681* (2013.01); *A61B 5/725* (2013.01); *A61B 5/7278* (2013.01); *A61B 5/7455* (2013.01); *A61B 5/742* (2013.01)

(56) References Cited

U.S. PATENT DOCUMENTS

| | | | |
|---|---|---|---|
| 9,314,170 | B2 | 9/2016 | Qasem |
| 9,730,622 | B2 | 8/2017 | Eisen et al. |
| 10,376,154 | B2* | 8/2019 | Koppel ............ A61B 5/6825 |
| 10,835,132 | B2 | 11/2020 | Qasem |
| 2009/0131804 | A1 | 5/2009 | Mukkamala et al. |
| 2010/0160794 | A1* | 6/2010 | Banet ............ A61B 5/14551 600/485 |
| 2011/0263989 | A1 | 10/2011 | Mukkamala et al. |
| 2012/0277602 | A1 | 11/2012 | Tichauer |
| 2013/0324809 | A1* | 12/2013 | Lisogurski ............ A61B 5/7285 600/323 |
| 2015/0087928 | A1* | 3/2015 | Podhajsky ............ A61B 5/01 600/479 |
| 2016/0058375 | A1 | 3/2016 | Rothkopf |
| 2016/0081563 | A1* | 3/2016 | Wiard ............ A61B 5/7278 600/485 |
| 2016/0220194 | A1 | 8/2016 | Kang et al. |
| 2017/0042435 | A1* | 2/2017 | Vermeulen ......... A61B 5/02416 |
| 2017/0086689 | A1 | 3/2017 | Shui et al. |
| 2017/0209055 | A1 | 7/2017 | Pantelopoulos et al. |
| 2017/0358239 | A1 | 12/2017 | Arney et al. |
| 2018/0279965 | A1 | 10/2018 | Pandit et al. |
| 2018/0296104 | A1 | 10/2018 | Qasem |
| 2019/0069835 | A1 | 3/2019 | Xu et al. |
| 2019/0101977 | A1 | 4/2019 | Armstrong-Muntner et al. |
| 2020/0008693 | A1 | 1/2020 | Mukkamala et al. |
| 2020/0033815 | A1 | 1/2020 | Bushnell et al. |
| 2020/0146563 | A1* | 5/2020 | Lee ......................... A61B 5/721 |
| 2021/0369129 | A1* | 12/2021 | Qasem ............... A61B 5/02427 |

OTHER PUBLICATIONS

Written Opinion dated Jul. 12, 2021 in co-pending PCT application PCT/IB2021/054655.

Liu et al., "Enhancing the robustness of smartphone photplethysmography: a signal quality index approach" Sensors, Mar. 30, 2020, vol. 20 No 7, pp. 1923-1939.

Moraes et al., "Advances in photopletysmography signal analysis for biomedical applications" Sensors, Jun. 9, 2018, vol. 18, pp. 1894-1920.

* cited by examiner

Inverted PPG Signal

1st Derivative of the
Inverted PPG Signal
✗ Peaks

WEARABLE DEVICE WITH PLETHYSMOGRAM SENSOR

BACKGROUND OF THE INVENTION

Aortic arterial blood pressure waveforms have waveform features that reflect the cardiovascular system status because of its proximity to the heart. These features are clinically important indicators of arterial and cardiac load and early independent predictive markers of cardiovascular events and diseases. However, recording high fidelity aortic blood pressure waveforms in the past accurately required an invasive procedure to insert a catheter with a pressure sensor inside the artery. As a result, non-invasive methods were created to estimate aortic pressure waveform with its cardiovascular related features from peripheral (e.g. radial, brachial) arterial pressure pulse recordings.

One of the most used and validated methods is the use of a transfer function to transform a high fidelity, non-invasively recorded peripheral pressure waveform into a central aortic pressure waveform with cardiovascular related features (Michael O'Rourke, "Method for ascertaining the pressure pulse and related parameters in the ascending aorta from the contour of the pressure pulse in the peripheral arteries", U.S. Pat. No. 5,265,011, Nov. 23, 1993). The transfer function is represented as the harmonic ratio between the input peripheral pressure waveform and the output central aortic pressure waveform. Instead of using a pressure to pressure transfer function, another method applied a different transfer function that converts a cuff acquired brachial arterial volume displacement waveform into the central pressure waveform with features (Ahmad Qasem, "Brachial Cuff" U.S. Pat. No. 9,314,170, Apr. 19, 2016). The brachial cuff had to be inflated to a set pressure value to record a consistent brachial volume displacement signal.

The estimated central pressure waveform and its features from these methods has been validated and has proven to provide clinically valuable indicators of arterial stiffness, heart load stress, arterial age, heart exercise capacity and predictors of cardiovascular risks. It is important to monitor, manage and control these measured features even if there are no symptoms. Providing data or information regarding these features to the general population will be useful and beneficial in monitoring cardiac health. However, currently these clinically significant features need to be measured in a clinical setting using medical devices that require meticulous tonometer recordings of a radial pulse signal or inflating a cuff to a set pressure to record brachial volume displacement pulse.

This invention addresses the accessibility of these features to the general population by transforming signals from a common wearable PPG (plethysmograph) sensor on mobile smartphones, fitness bands or smartwatches into a central aortic pressure waveform with cardiovascular related features similar to the outputs of the methods by O'Rourke and Qasem patents. This new method applies a transfer function that converts a PPG signal from the finger into a central pressure waveform signal. Then, calculates features from the central pressure waveform and displays them as cardiac health indicators to guide users in monitoring their health on a frequent basis.

The aim of the invention is to process, and transform a common wearable smart watch or mobile PPG sensor signal into a central aortic pressure pulse with cardiovascular related features in order to display these health indicators to guide the general users in maintaining and managing their cardiac health.

SUMMARY OF THE INVENTION

The invention is directed to a method of monitoring central blood pressure parameters using a PPG sensor desirably on a smart watch or smart band, but aspects of the invention can also be useful for embodiments employing a laptop or mouse. The smart watch or smart band is constructed to have a microcontroller unit (MCU) and a PPG sensor adapted to sense blood perfusion in the finger (e.g., an index finger) of the person wearing the smart watch or smart band. It has been discovered that sensing blood perfusion in the finger results in a signal in which cardiovascular features can be detected after proper filtering and processing. On the other hand, cardiovascular features cannot be detected, at least reliably, by placing the backside of the wrist against a PPG sensor. Features shown by the arrows 100 in FIG. 8 show an example of an inverted finger PPG pulse and an inverted upper wrist PPG pulse. The inverted finger PPG pulse has features as shown by the arrows while the inverted upper wrist PPG pulse is featureless.

The PPG sensor outputs a raw, analogue PPG signal when the user places their finger against an exposed optical portion of the PPG sensor. In some embodiments, the PPG sensor is embedded in the housing of the smart watch or smart band and the optical portion of the PPG sensor is exposed through the side wall and/or the bezel on the side wall of the smart watch or smart band. The optical portion of the PPG sensor can be flush with the surface of the housing, but it is desirable for the optical portion to be recessed or raised with respect to the housing surface. The raising or recessing of the optical portion provides tactile feedback to user so they can easily ensure that the finger covers the optical portion of the PPG sensor completely. In other embodiments, the PPG sensor can be attached to a wristband connected to the smart watch or smart band with the optical portion of the PPG sensor exposed outward from the wristband. In other embodiments, the PPG sensor can be located on the face of the watch or the electronics module of a smart band. The user places their finger against the PPG sensor for a period of time greater than about 5 secs, in order to capture several cycles. The PPG sensor outputs a raw, analogue PPG signal to the MCU on the smart watch or smart band. The MCU, or other electronic circuitry on the smart watch or smart band, converts the raw, analogue PPG signal to a digitized signal. This digitized signal is desirably processed on the smart watch or smart band using its MCU, although it is possible to implement the invention using the Cloud. If the Cloud is used, then the digitized signal is transmitted from the smart watch or smart band to the Cloud for further computing. The MCU on the smart watch or smart band can process data before transmitting the data to the Cloud. In addition, it is possible to implement some of the digital processing on a smart phone associated with the smart watch or smart band, or a combination of a smart phone and the Cloud.

The digitized signal is processed through a low pass filter and a high pass filter. The purpose of the high pass filter is to remove drift from the signal. The purpose of the low pass filter is to remove noise, but it is important that the low pass filter does not filter out relevant physiological data. The digitized signal must be inverted after it is processed through the low pass and high pass filters. The filtered finger PPG signal is inversely proportional to the volume of blood in the finger. It is important to find the part of the wave corresponding to the foot of the central aortic pressure waveform. The reason of the inversion is that the filtered finger PPG has negative slope at the start of the pulse while pressure signal has positive slope (upstroke). By inverting the PPG signal, the finger PPG and the pressure pulse will have similar features which is important when estimating the transfer function. Transfer functions tend to be more stable if the input and output signals have common, aligned features. The next step is to detect individual pulses in the digitized PPG signal after it has been filtered and inverted. Then, several individual pulses are averaged to produce an average, un-calibrated PPG pulse.

A transfer function or a combination of transfer functions is applied to the average, un-calibrated PPG pulse to generate an un-calibrated aortic pressure waveform with cardiovascular waveform features preserved. The preserved cardiovascular waveform features of the un-calibrated aortic pressure waveform comprising a first shoulder, a second shoulder and an incisura, see e.g., FIG. 7. The one or more generalized transfer functions represent the harmonic ratio in amplitude and phase to transform an average, un-calibrated PPG pulse into the un-calibrated aortic pressure waveform with cardiovascular related features preserved. In one embodiment, there are two transfer functions: one that converts the average PPG pulse into an un-calibrated, radial pressure pulse, and a second transfer function that converts the un-calibrated, radial pressure pulse into the un-calibrated central aortic pulse. In another embodiment, one transfer function that converts the average PPG pulse to the un-calibrated central aortic pulse.

The next step is to detect waveform features in the un-calibrated aortic pressure waveform, and calculate parameters pertaining to the un-calibrated aortic pressure waveform. Useful parameters may include ratios such as the area under the systolic curve divided by the area under the diastolic curve, or the ratio of systolic pressure at the first and second shoulder in relation to overall height, or the ratio of the peripheral pressure waveform height to the central pressure waveform height, or other parameters or calculated values such as an overall score. One or more of the calculated parameters or an indication of said calculated parameters are displayed on the smart watch or smart band, for the user to view conveniently.

Depending on the location of the PPG sensor it may be also able to sense blood perfusion by placing the palm side of the wrist against the sensor. More specifically, using the PPG sensor to measure perfusion in the main radial artery from the lower wrist can result in a waveform exhibiting cardiovascular features if measured properly. For example, using a wristband with a PPG sensor resting against the lower or palm side wrist in the appropriate position is a possibility. It has been discovered that sensing blood perfusion by placing a PPG sensor against the lower wrist to measure blood perfusion through the main radial artery results in a signal in which cardiovascular features can be detected after proper filtering and processing. Of course, a transfer function for converting the PPG signal from the lower or palm side wrist must be determined separately from a transfer function for converting a PPG signal from a finger.

Additional embodiments of the invention include placing a PPG sensor on a laptop computer or a mouse. In the laptop embodiment, the PPG sensor can be located on the keyboard or in a location separated from keyboard and track pad. The user can place his/her (index) finger on the PPG sensor for measurement. In the mouse embodiment, the PPG sensor can be located on one of the mouse buttons, where the (index) finger is naturally placed.

DETAILED DESCRIPTION OF THE DRAWINGS

Figure 1:
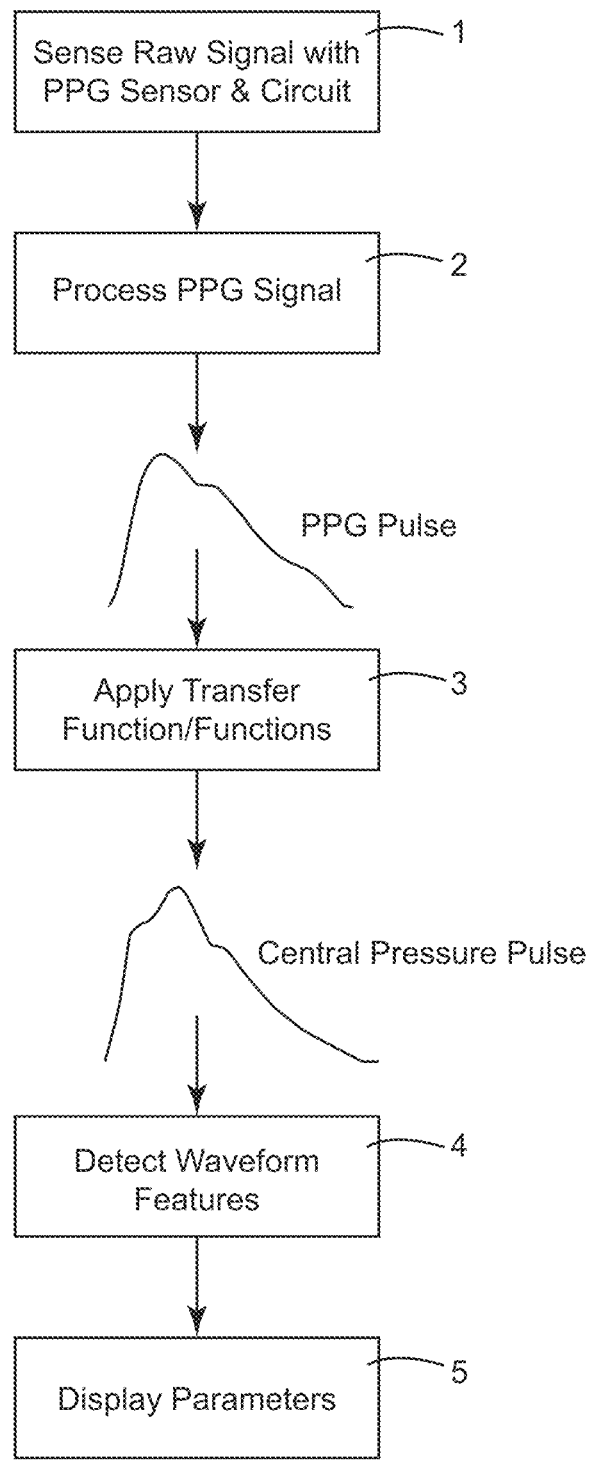
FIG. 1 is a flow chart illustrating the steps involved in using a PPG sensor to sense blood perfusion in a finger, and processing the signal in part using the transfer function method to result in an un-calibrated central pressure pulse from which cardiovascular features are detected and parameters displayed, e.g. on a smart watch.

FIG. 1 shows the general steps of implementing invention. In general, the first step, block 1, is to sense a raw signal with a PPG sensor designed to measure a PPG signal from a finger or wrist. Preferably, the PPG sensor is configured to measure a PPG signal from the user's index finger. The PPG sensor is desirably located on a smart watch or smart band, but can be located on a laptop, on a mouse or tethered to an electronic device such as a smart phone. The second step, block 2, is processing the raw signal which results in a PPG pulse as shown in FIG. 1. The third step, block 3, is to apply one or more transfer functions to produce an aortic pressure waveform, which is shown in FIG. 1 as a central pressure pulse. The fourth step, block 4, is to detect waveform features in the central aortic pressure waveform and calculate one or more clinically significant parameters including a summary score. The fifth step, block 5, is to display the calculated parameters and the summary score, e.g. on the display of the smart watch or smart band, or on another display.

The PPG sensor unit consists of one or more LED light sources, e.g. green, red or infrared, photodetectors and the necessary circuitry to drive the LEDs and the photodetectors. The PPG sensor unit contains two portions: optical and electrical. The optical portion is made up of transparent material(s) that allows light to be passed through from PPG sensor unit to a human, and from a human to the PPG sensor unit. The optical portion of the PPG sensor unit can be extended using light pipe(s).

The PPG sensor unit can be embedded inside a wearable device such as a smart watch or smart band. The PPG signals can be sent to the MCU (microcontroller unit) or the Cloud or to a smart phone for further processing & calculations. The PPG sensor package can be designed to run in reflectance or transmission mode.

Figure 2:
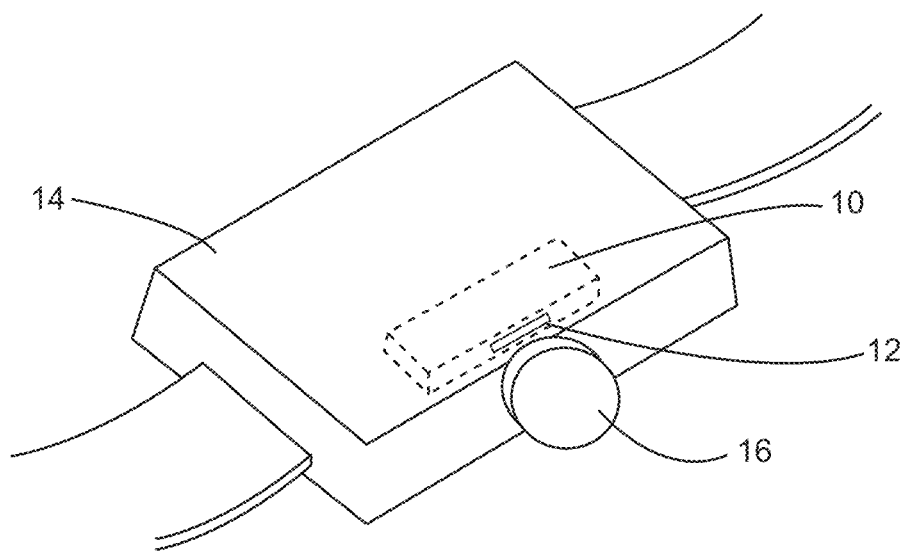
FIG. 2 is schematic drawing of one embodiment a smart watch having an embedded PPG sensor with the optical element exposed through the bezel or crown of the watch.

FIG. 2 illustrates one embodiment of a smart watch 14 implementing the invention. In FIG. 2, the PPG sensor unit 10 is embedded in a watch 14 with the optical portion 12 facing the crown or bezel 16. The user places a finger, such as the index finger, on the crown 16 to record the raw finger PPG pulse.

Figure 3:
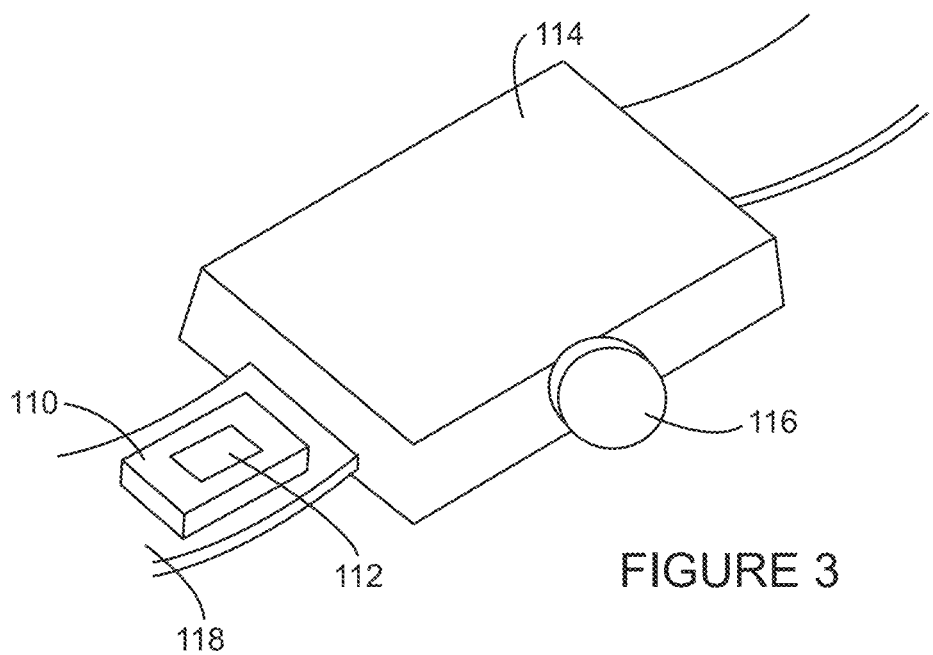
FIG. 3 is schematic drawing of another embodiment a smart watch having a PPG sensor mounted on the watch band, with the optical element exposed upward from the band.

FIG. 3 illustrates another embodiment of a smart watch 114 implementing the invention. The PPG sensor unit 110 is on the wristband 118 with the optical portion 112 facing upward and exposed next to the body of the smart watch 114. The user places a finger, such as the index finger, on the optical portion 112 to record the raw finger PPG pulse.

Figure 4:
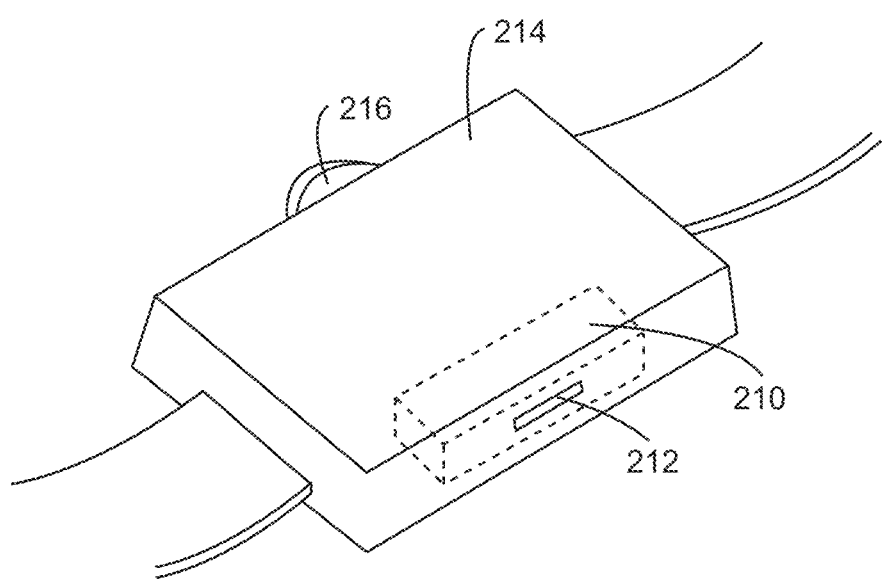
FIG. 4 is schematic drawing of another embodiment of a smart watch having an embedded PPG sensor with the optical element exposed through the sidewall of the watch housing opposite the bezel.

FIG. 4 illustrates another embodiment of a smart watch 214 implementing the invention. The PPG sensor unit 210 is embedded in a watch housing 214 with the optical portion 212 facing away from the bezel 216 of the watch 214. The user places a finger, such as the index finger, against the optical portion 212 to record the raw finger PPG pulse.

Figure 4A:
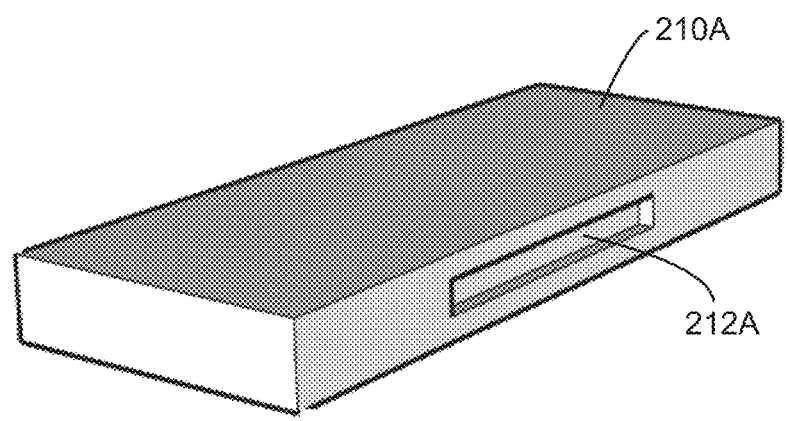
FIG. 4A shows a PPG sensor with a recessed optical portion.
Figure 4B:
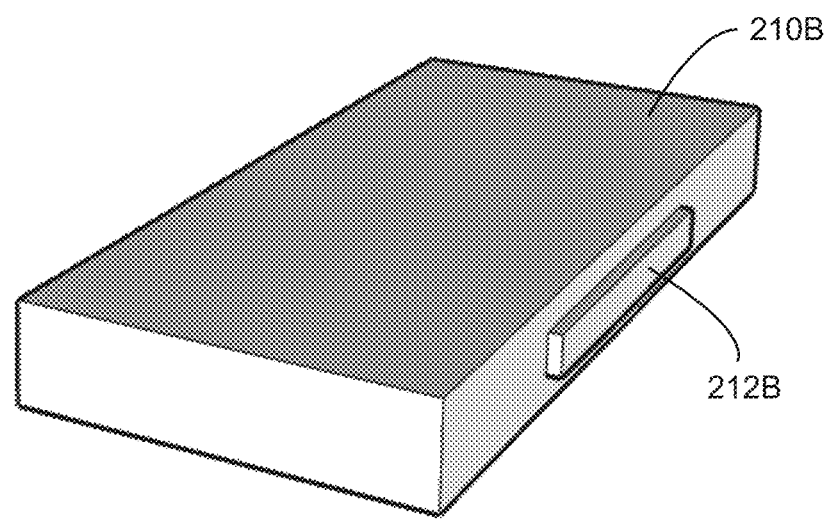
FIG. 4B shows a PPG sensor with a raised optical portion.

FIG. 4A shows a PPG sensor 210A with a recessed optical portion 212A. FIG. 4B shows a PPG sensor 210B with a raised optical portion 212B. The recessed 212A and raised 212B portions provide tactile feedback to the user for locating their finger over the optical portion of the PPG sensor. The tactile feedback helps the user to cover the exposed optical portion of the PPG sensor 212 fully, which maximises the amount of reflected light from the measurement finger, and improves system reliability and accuracy.

Figure 5:
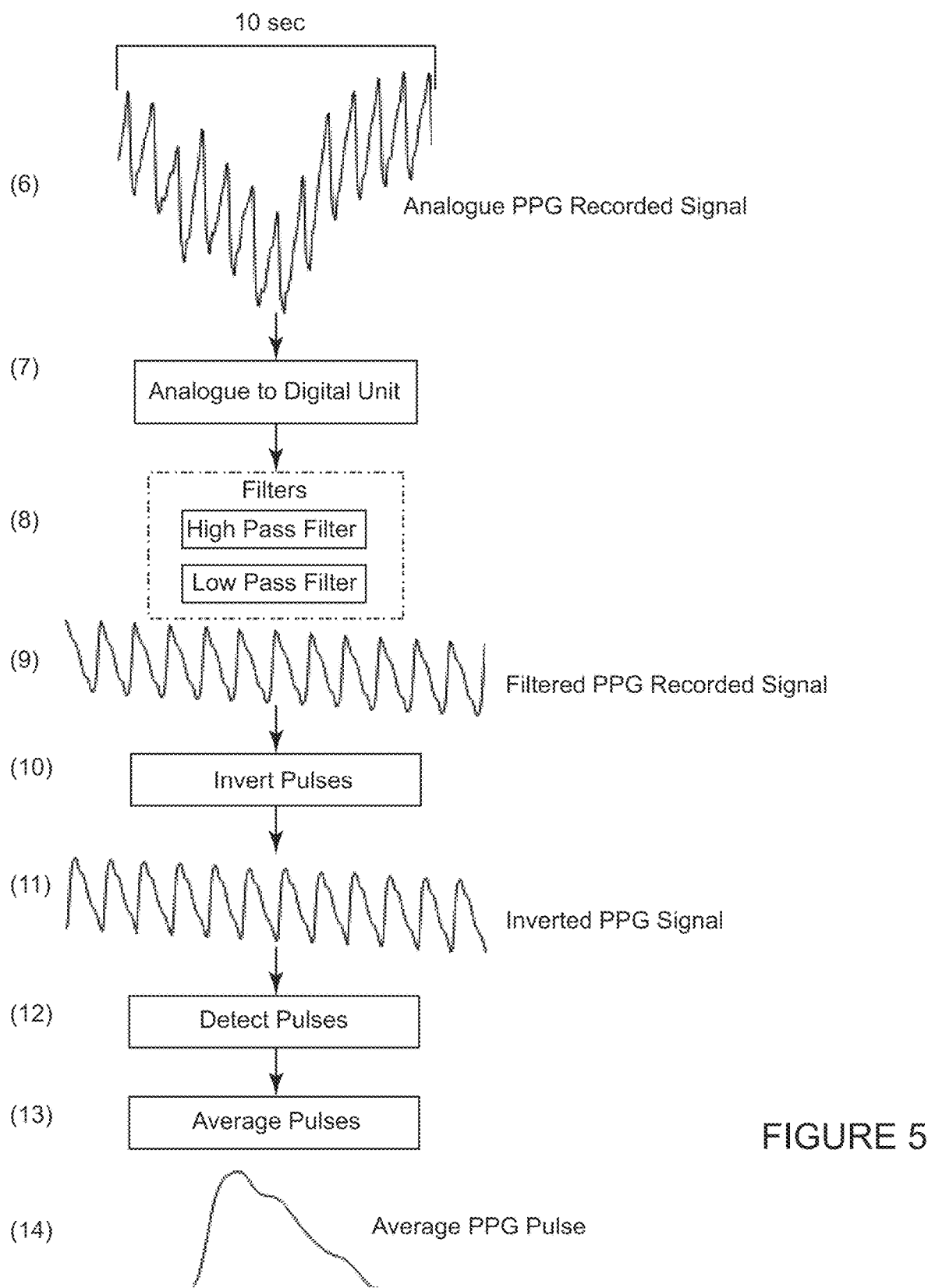
FIG. 5 is a flow chart illustrating the steps involved with sensing the PPG signal, and processing the signal in order to result in an average PPG pulse, which in turn is converted to a central pressure pulse using the transfer function method.

FIG. 5 shows digital processing steps for processing the raw PPG signal (6). The raw PPG recorded signal (6) is an analogue signal, which can have a duration of 5 seconds or more, and is transmitted from the PPG sensor to the smart watch or smart band for digital signal processing on preferably on the MCU on the smart watch or smart band, or on an associated smart phone, and some processing can occur in the Cloud as well. The signal processing steps shown in FIG. 5 include converting the analogue signal to digital signal (7) via an A/D converter, filtering the digital signals (8) through a high pass and a low pass filter, inverting the filtered digital PPG signal (10), detecting the pulses in the inverted PPG signal (12), and (13) averaging the PPG pulse. All these steps and calculations can be implemented in an MCU or on the Cloud.

Referring still to FIG. 5, the A/D converter (7) digitizes the raw, analogue PPG signal (6) and samples the signal at a sampling frequency (fs) not less than a 100 Hz. Then, a high pass filter is applied to the digitized signal to reduce signal baseline drift and a low pass filter is applied to remove high frequency artifacts noise, see step (8). For the high pass filter, the stop frequency can be between 0.003-0.05 Hz and the pass frequency can be between 0.95-1.05 Hz. An example of a high pass filter is a Butterworth high pass filter with a −50 dB stop frequency of 0.01 Hz, a −3 dB pass frequency of 1 Hz. The low pass filter will have a −3 dB frequency between 30 to 50 Hz. Both filters should have low phase delay. Both filters are applied to the digitized signals producing the filtered PPG signal (9).

Then, the filtered PPG signal is inverted, see step (10), by implementing the following equation $$\text{InvPPGSig} = -\text{PPGSig} \qquad 1$$

where PPGSig is the filtered PPG signal (9) and InvPPGSig is the inverted PPG signal (11). Inversion of the filtered PPG signal is required because the central pressure pulse starts with an upstroke (high positive slope line) indicating cardiac ejection while the recorded, filtered finger PPG pulse starts with a negative slope line. Since the aim is to produce a central pressure pulse, it is important to have similar start features on the two pulses. Accordingly, the finger PPG pulse is inverted to have an upstroke feature at the start of the pulse like in the central pressure pulse.

Figure 6:
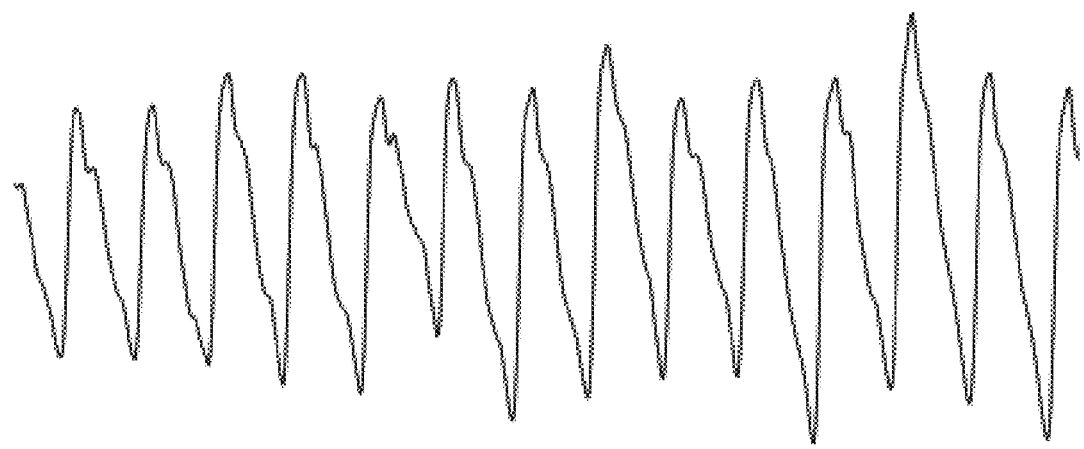
FIG. 6 is a schematic drawing illustrating aspects of how to detect the beginning of the upstroke in the inverted PPG signal.
Figure 6:
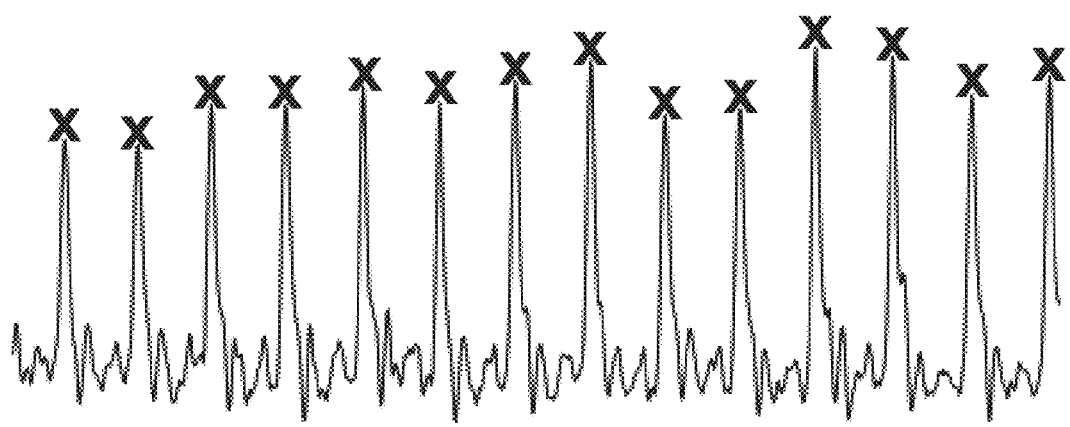

The next step (12) is to detect the start and the end of each pulse in the inverted PPG signal (11). The start of the pulse is determined by calculating the $1^{st}$ derivative and identifying the peaks, see FIG. 6, which corresponds to the pulse upstroke at the pulse start. After the pulses are detected (12), a number of signal pulses are produced, e.g. 10 pulses. Averaging these pulses produces one average PPG pulse, see step (14) in FIG. 5.

The average PPG pulse (14) is the inputted in to one or more transfer functions, see step 3 in FIG. 1, to produce an average central pressure waveform with cardiovascular features preserved. The transfer function represents the harmonic ratio in amplitude and phase between the input and the output signals. The equation of the transfer function can be written in a frequency or time domain format. The PPG waveform to aortic pressure transfer function is determined beforehand from simultaneous recordings of PPG waveform and invasive (e.g. catheter) or an equivalent non-invasive (e.g. SphygmoCor) aortic pressure waveforms. The estimation involves either frequency harmonics analysis or estimating coefficients for the impulse response. The transfer function can be represented and written in the following frequency domain format a) Amplitude $$|H_{a \to b}(f)| = \left| \frac{Sig_b(f)}{Sig_a(f)} \right| \qquad 2$$

where $|H_{a \to b}(f)|$ is the transfer function frequency amplitude ratio of $Sig_b$ to $Sig_a$ $Sig_a$ is the input signal in frequency domain
$Sig_b$ is the output signal in frequency domain, and
f is the frequency which will range from 0 to fs/2 in Hz.
b) Phase $$\text{Phase}(H_{a \to b}(f)) = \text{Phase}(Sig_b(f)) - \text{Phase}(Sig_a(f)) \qquad 3$$

Where Phase $(H_{a \to b}(f))$, is the angle of $H_{a \to b}(f)$ at frequency f.
Phase $(Sig_a (f))$ is the angle of $Sig_a$ at frequency f, and
Phase $(Sig_b (f))$ is the angle of $Sig_b$ at frequency f.

In the time domain, the transfer function can be represented as an impulse response or a set of coefficients that when converted into frequency domain would be equivalent to $H_{a \to b}(f)$.

$$Imp_{a \to b}(t) = IFFT[H_{a \to b}(f)] \qquad 4$$

where Imp(t) is the impulse response in time domain,
IFFT is the inverse fast Fourier transform, and
t is the time from 0 to pulse length time in millisecond.

Assume $Sig_b$ to be the central aortic pressure waveform in frequency domain and $Sig_a$ to be the average PPG signal (14) in frequency domain.

$$AoPW(t) = FFT(Sig_b(f)) \qquad 5$$

$$PPG(t) = FFT(Sig_a(f)) \qquad 6$$

where AoPW(t) is the central aortic pressure waveform in time domain,
PPG(t) is the average PPG pulse (14), and
FFT is fast Fourier transform.

The calculation of an aortic pressure waveform from a PPG pulse (14) using the transfer function can be made in frequency or time domain. First, in frequency domain, the aortic pressure in frequency can be calculated as $$Sig_b(f) = H_{a \to b}(f) \times Sig_a(f) \qquad 7$$

where $Sig_b$ (f) can be converted into an aortic pressure waveform in the time domain AoPW(t) using the inverse fast Fourier transform (IFFT)

$$AoPW(t) = IFFT[Sig_b(f)] \qquad 8$$

To calculate AoPW(t) in the time domain, uses the following equation $$AoPW(t) = Imp_{a \to b}(t) * PPG(t) \qquad 9$$

where * is the convolution operation.

Alternatively, an intermediate transfer function that transforms the PPG waveform to a radial pressure waveform can be determined beforehand from simultaneous recordings of PPG waveform and radial pressure waveforms using a tonometer. The intermediate transfer function can be determined using similar techniques as described above. Then, the data representing the radial pressure waveform can be input in to a transfer function that converts the radial pressure waveform into a central aortic pressure waveform as is known in the art.

Figure 7:
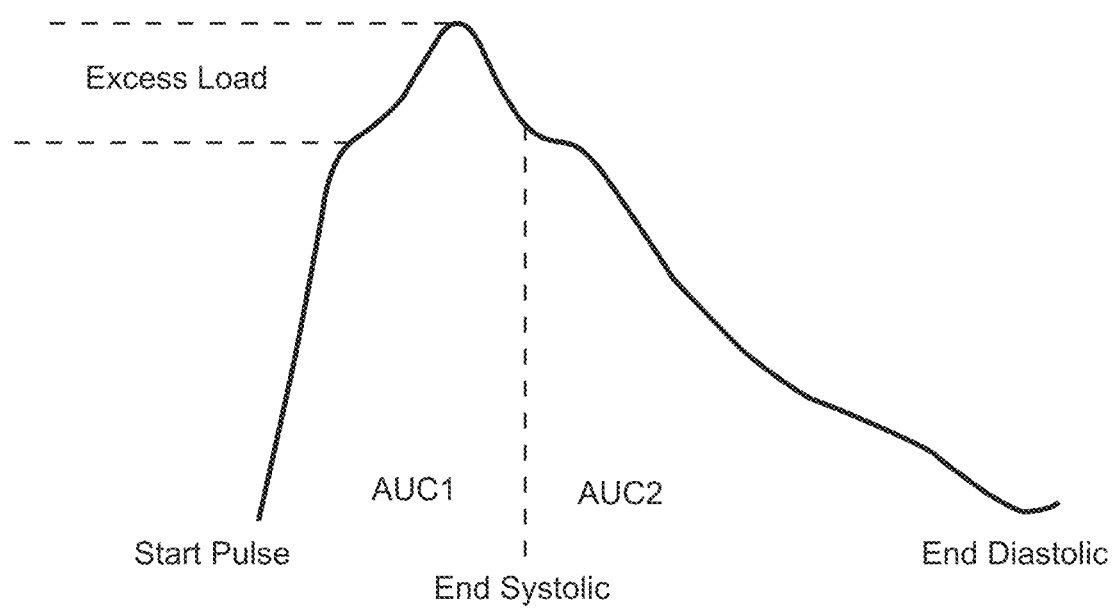
FIG. 7 is a schematic drawing illustrating waveform features detected in the un-calibrated central aortic pressure waveform.
Figure 8:
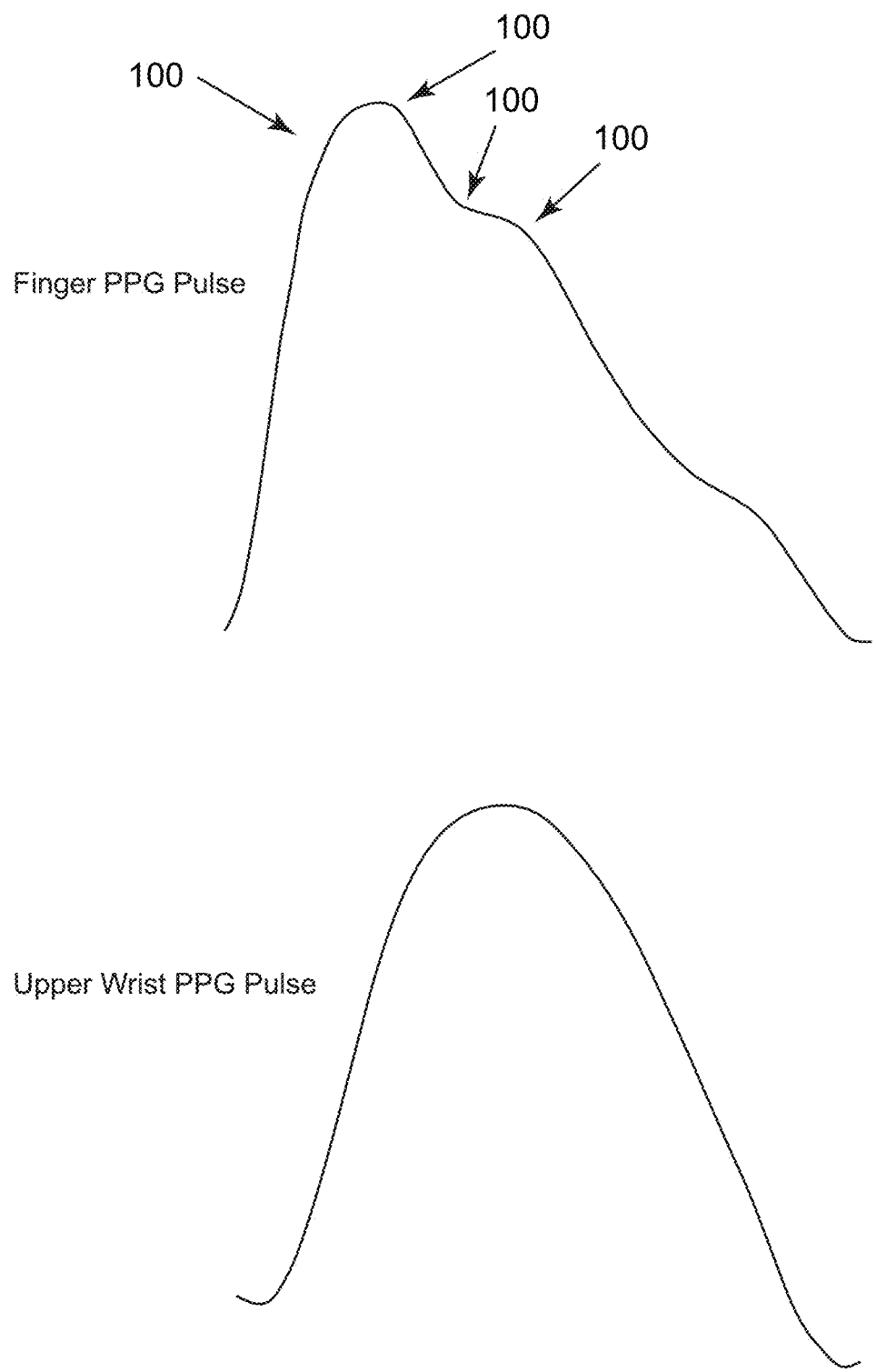
FIG. 8 is a drawing comparing a filtered, inverted PPG signal from a finger compared to a filtered, inverted signal from the back side of the wrist.

FIG. 7 shows the central aortic pressure waveform with features resulting from the application of the one or more transfer functions. As indicated in box 4 of FIG. 1, software is configured to detect the features shown in FIG. 7. The software applies the $1^{st}$ derivative method to detect the incisura after the peak. The incisura will be the first zero crossing of the $1^{st}$ derivative after the aortic pulse peak. The incisura represents the end of systolic phase (heart ejection) and the start of diastolic phase (heart blood filling). Detecting the $1^{st}$ and $2^{nd}$ systolic peak provides an estimate of the extra load at the heart since the $2^{nd}$ peak is a result of reflected pressure that add to the load at the heart. The software can also be configured to calculate the area under the systolic curve (AUC1), as shown in FIG. 7, representing heart's work during pumping which also reflects the body's demand for oxygenated blood. The software can be configured to calculate the area under the diastolic curve (AUC2), as shown in FIG. 7, representing heart's work during ventricular filling which also reflects the heart supply of oxygenated blood. The ratio of AUC2 to AUC1, which also a ratio of oxygenated blood supply to body demand, has shown to be related to physical fitness and endurance. These parameters as shown in FIG. 7 are displayed, e.g., on the display of smart watch or smart band as health indicators to help users monitor their health.

Figure 9:
FIG. 9 is a display for a smart watch, in which the software displays indications of calculated waveform parameters from the un-calibrated central pressure pulse and/or the un-calibrated peripheral pressure pulse.

FIG. 9 shows a display for a smart watch (or other display such as a display on a smart band) in which software displays indications of heart parameters calculated from the un-calibrated average central pressure pulse. The label "Heart Stress" is calculated as the difference between the 1st and 2nd systolic peak in relation to the pulse height. The arrows 20 in FIG. 9 are pointed in the green area which means that the calculated parameter is good. The displayed "Heart Age" is correlated to healthy cardiovascular age by calculating the amplification ratio, namely the ratio of the peripheral pulse height to central pulse height, and comparing the amplification ratio to a published healthy population study. The label "Exercise Capacity" is the ratio of the diastolic area under the curve to the systolic area under the curve. The overall score (ARTY) is based on a combination of the detected heart features.

Figure 10:
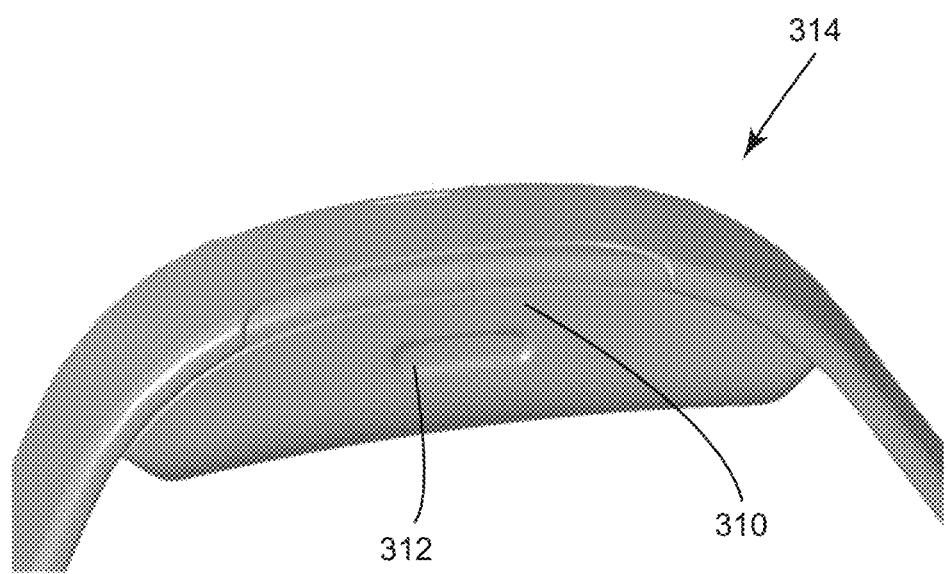
FIG. 10 is schematic drawing of an embodiment a smart band having an embedded PPG sensor with the optical element exposed along the side of the housing for the electronics module.

FIG. 10 is schematic drawing of an embodiment a smart band 314 having an embedded PPG sensor 310 with the optical element 312 exposed along the side of the housing for the electronics module. Although not shown, the smart band 314 can have visual indications, e.g. LEDs, but does not necessarily have a UI (user interface) screen. If it does have a display screen, then information similar to that shown in FIG. 9 can be displayed. If not, then the visual indicators need to be adapted, or the information/data can be transmitted to another device for display and possibly further processing.

Figure 11:
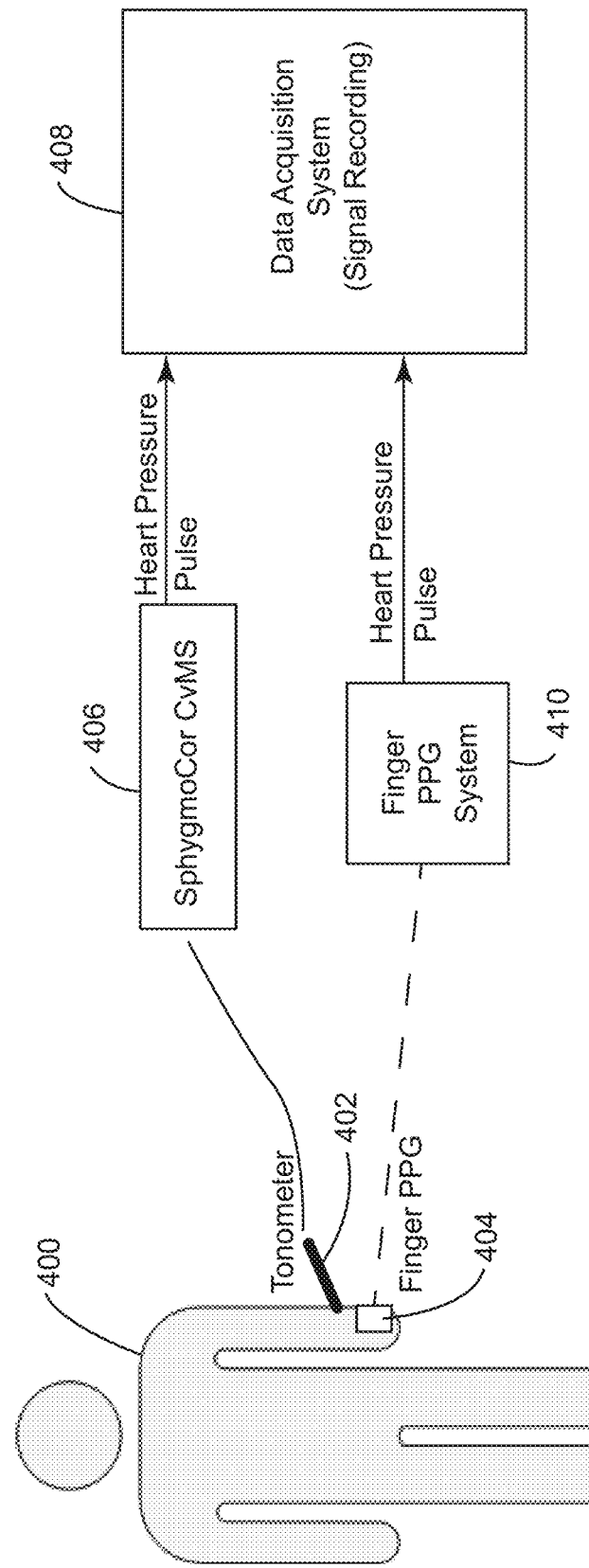
FIG. 11 is a schematic drawing illustrating the set up for testing the accuracy of the invention compared to the accuracy of the SphygmoCor® system.

The accuracy of the invention was tested against the SphygmoCor® system for generating a central aortic pressure pulse based on a non-invasive peripheral blood pressure waveform measurement. The SphygmoCor® system is the commercial embodiment of the system described in the above referenced O'Rourke patent, U.S. Pat. No. 5,265,011, is FDA-cleared and is considered to be the gold standard for non-invasive measurement of central aortic pressure waveforms. FIG. 11 is a schematic drawing illustrating the set up for testing the accuracy of the invention compared to the SphygmoCor® system. Several recordings (3 to 9) were taken from thirteen subjects (4 female, 9 male), ages 20-65, for 10 second durations. The subjects provided a wide range of central aortic pressure waveform shapes (young, old, healthy, unhealthy). Referring to FIG. 11, a tonometer 402 was used to measure the radial pressure pulse of the subject 400 in accordance with known techniques. At the same time, a PPG sensor 404 was used to take measurements of the subject's index finger. The signal from the tonometer 402 was transmitted to a SphygmoCor® system 406 and the central pressure waveform data outputted from the SphygmoCor® system 406 was recorded in data acquisition system 408. Contemporaneously, the signal from the PPG sensor 404 was transmitted to a system 410 constructed in accordance with the current invention, and the central pressure waveform data outputted from the system 410 was also recorded in data acquisition system 408.

Figure 12A:
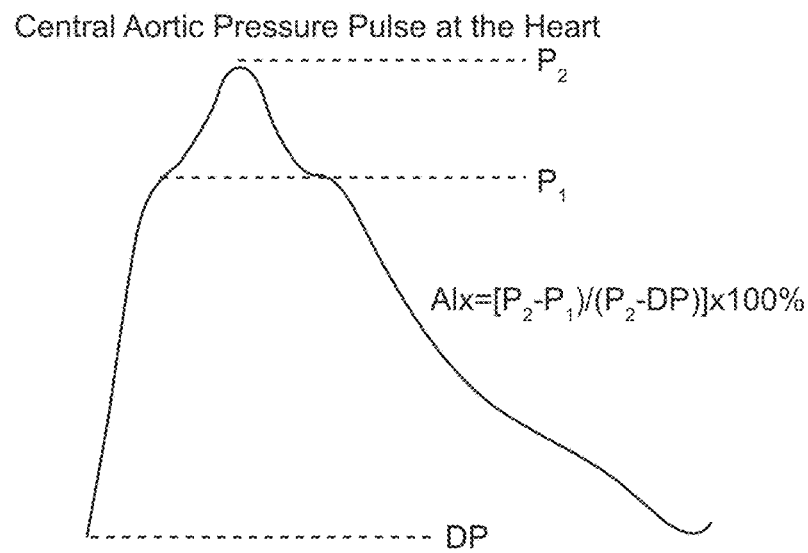
FIGS. 12A and 12B illustrate the calculation and comparison of the augmentation index on data collected for the invention and the SphygmoCor® system.
Figure 12B:
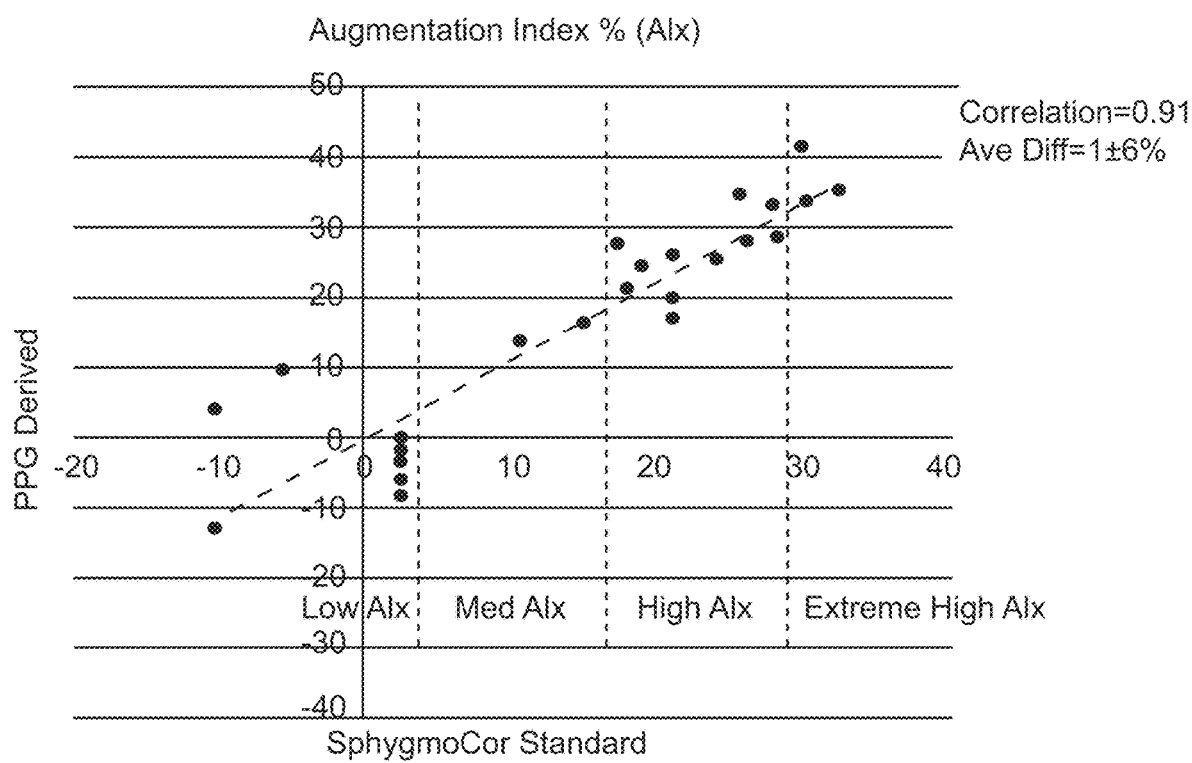

FIG. 12A illustrates a central aortic pressure waveform and parameters identified and used to calculate the augmentation index (AIx). FIG. 12B is plot comparing the calculated augmentation index (AIx) for central aortic pressure waveforms derived on data collected using the invention with a PPG sensor and augmentation index (AIx) for central aortic pressure waveforms derived on data collected using the SphygmoCor® system. The correlation is 0.91 overall and appears even tighter for higher values of AIx.

Figure 13A:
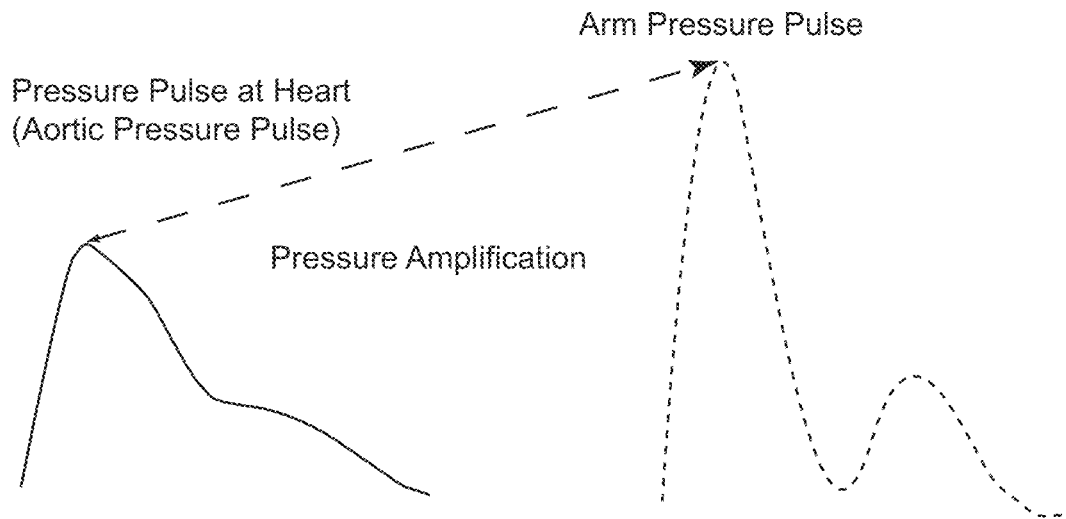
FIGS. 13A and 13B illustrate the calculation and comparison of pressure amplification on data collected for the invention and the SphygmoCor® system.
Figure 13B:
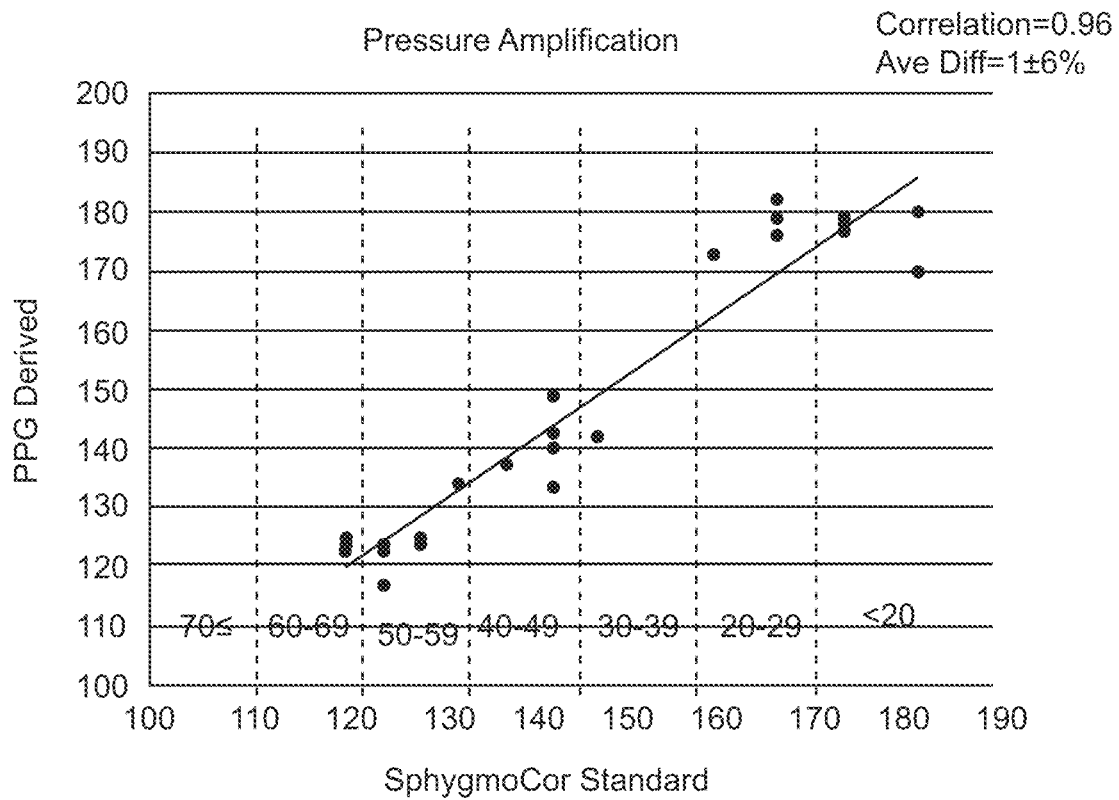

FIG. 13A illustrates pressure amplification between the central pressure waveform (heart) and the peripheral pressure waveform (wrist or finger). FIG. 13B is plot comparing the calculated pressure amplification for central aortic pressure waveforms derived on data collected using the invention with a PPG sensor to detect pressure in the finger and pressure amplification for central aortic pressure waveforms derived on data collected using the SphygmoCor® system and a tonometer to measure radial pressure waveforms. The correlation is 0.96 overall.

Figure 14A:
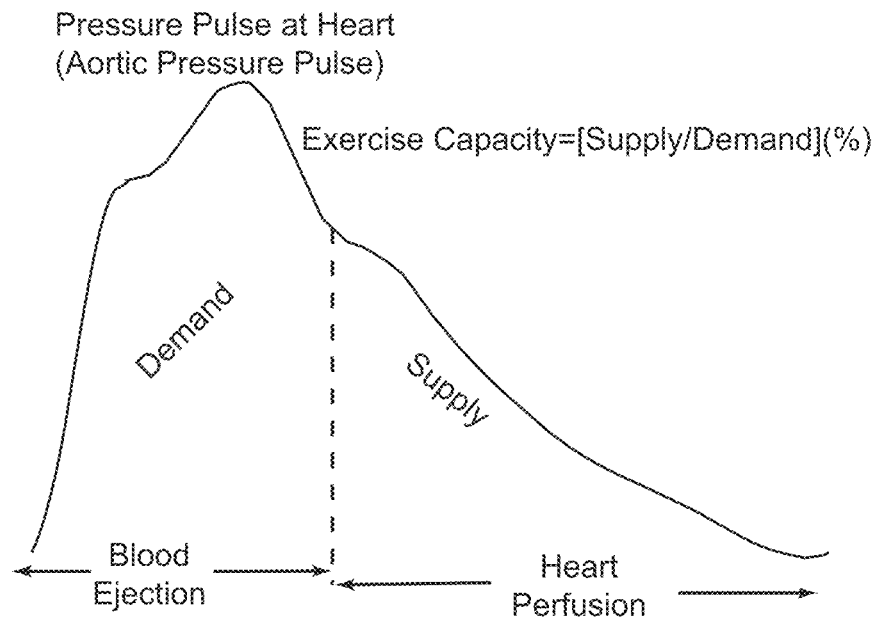
FIGS. 14A and 14B illustrate the calculation and comparison of exercise capacity on data collected for the invention and the SphygmoCor® system.
Figure 14B:
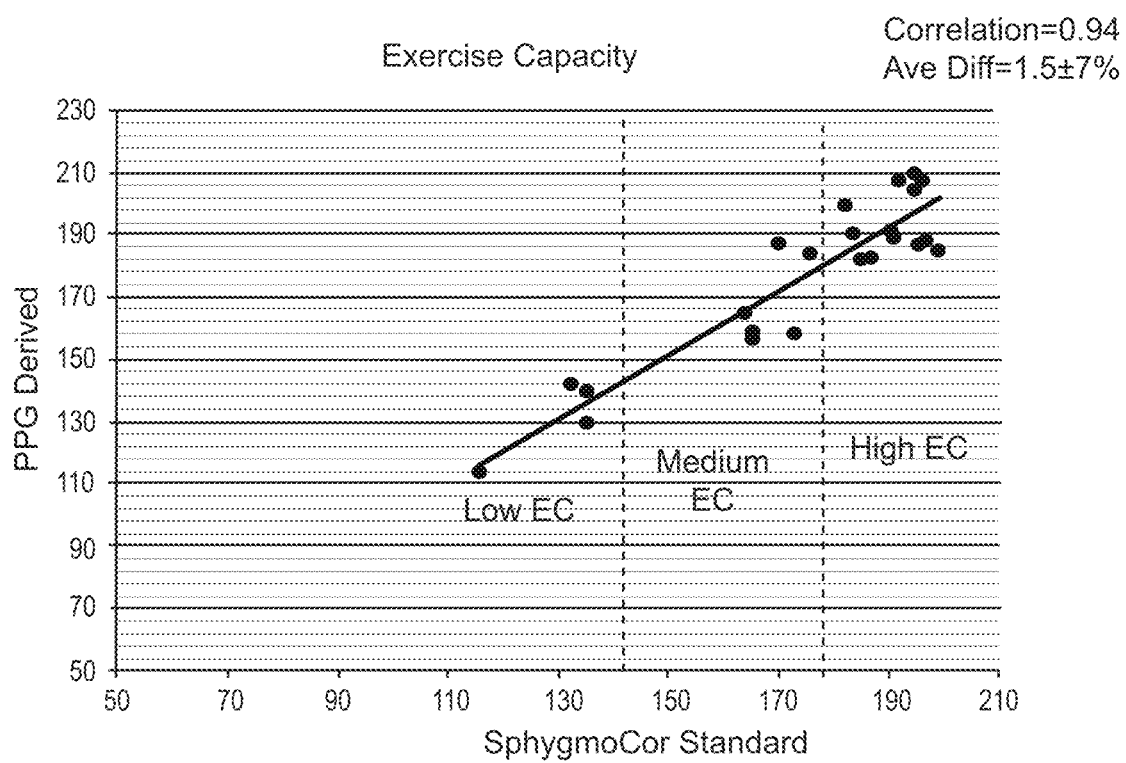

FIG. 14A illustrates a central aortic pressure waveform and parameters identified and used to calculate exercise capacity (EC). FIG. 14B is plot comparing the calculated exercise capacity (EC) for central aortic pressure waveforms derived on data collected using the invention with a PPG sensor to detect pressure in the finger and exercise capacity (EC) for central aortic pressure waveforms derived on data collected using the SphygmoCor® system and a tonometer to measure radial pressure waveforms. The correlation is 0.94 overall.

Figure 15A:
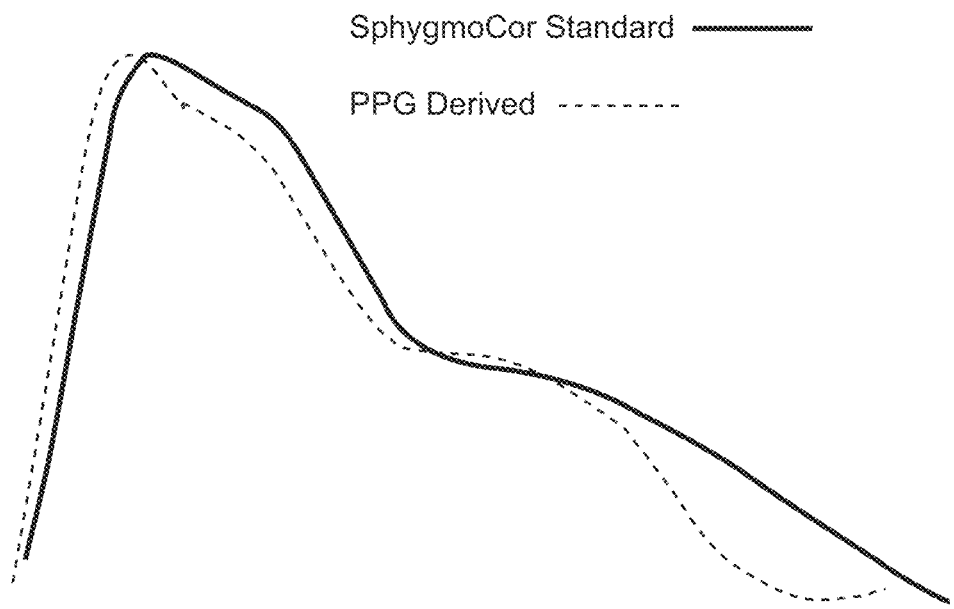
FIG. 15A shows the comparison of a central aortic waveform of a healthy person generated using the invention compared to the central aortic waveform generated using the SphygmoCor® system.
Figure 15B:
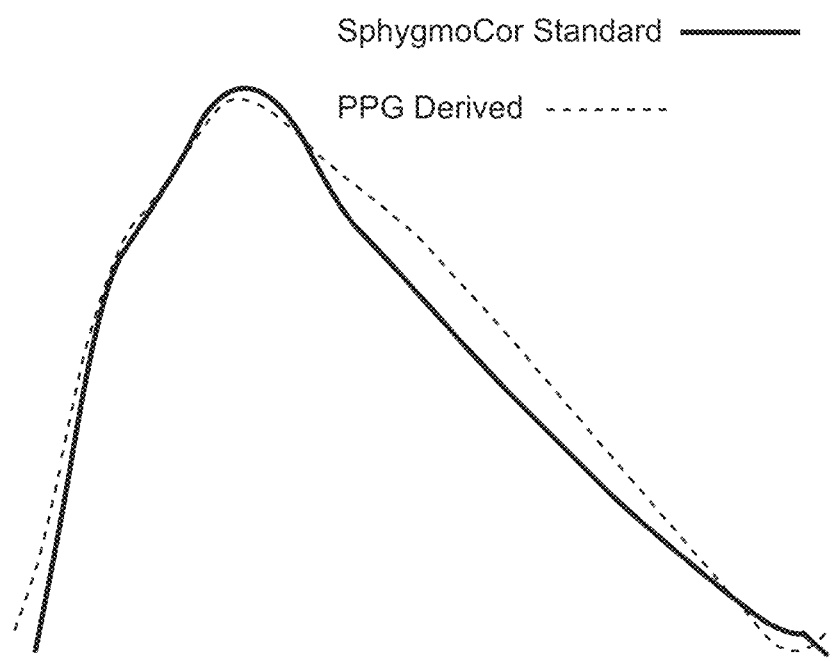
FIG. 15B shows the comparison of a central aortic waveform of an unhealthy person generated using the invention compared to the central aortic waveform generated using the SphygmoCor® system.

FIG. 15A shows the comparison of a central aortic waveform of a healthy person generated using the invention compared to the central aortic waveform generated using the SphygmoCor® system. FIG. 15B shows the comparison of a central aortic waveform of an unhealthy person generated using the invention compared to the central aortic waveform generated using the SphygmoCor® system.

As mentioned, the invention can also be implemented by placing the lower wrist or palm side against a PPG sensor to measure blood perfusion. While the transfer function or transfer functions must accommodate the different location for obtaining the input data, other aspects of digital signal processing (filtering, inversion, detection of waveform foot, conversion to un-calibrated central pressure waveform, detection of waveform features, calculating parameters and display on smart watch) should be similar to those described above with respect to the finger.

What is claimed is:

1. A method of monitoring central blood pressure parameters comprising the steps of:
   providing a wearable smart watch or smart band having a microcontroller unit (MCU) and a PPG sensor adapted to sense blood perfusion in the finger of the person wearing the smart watch or smart band, said PPG sensor outputting a raw, analog PPG signal when the user places their finger against an exposed optical portion of the PPG sensor;
   placing the user's finger against the exposed optical portion of the PPG sensor for a period of time sufficient to sense several blood pulses, and outputting a raw, analog PPG signal to the MCU;
   converting the raw, analog PPG signal to a digitized signal;
   processing the digitized signal through a low pass filter and a high pass filter;
   inverting the digitized signal after it has been processed through the low pass and high pass filters;
   detecting individual pulses in the digitized PPG signal after it has been filtered and inverted;
   averaging several individual pulses to produce an average, un-calibrated PPG pulse;
   applying one or more generalized transfer functions to the average, un-calibrated PPG pulse to generate an un-calibrated aortic pressure waveform with cardiovascular waveform features preserved, said preserved cardiovascular waveform features of the un-calibrated aortic pressure waveform comprising a first shoulder, a second shoulder and an incisura, said one or more generalized transfer functions representing a harmonic ratio in amplitude and phase to transform the average, un-calibrated PPG pulse to the un-calibrated aortic pressure waveform with cardiovascular waveform features preserved;
   detecting waveform features in the un-calibrated aortic pressure waveform and calculating parameters pertaining to the un-calibrated aortic pressure waveform; and
   displaying one or more of said calculated parameters or an indication of said calculated parameters.

2. The method as in claim 1 wherein the PPG sensor is embedded in the housing of the smart watch or smart band and the optical portion of the PPG sensor is exposed through a side wall of the housing or a bezel on the side wall of the housing.

3. The method as in claim 1 wherein the PPG sensor is attached to a wrist band connected to the smart watch or smart band and the optical portion of the PPG sensor is exposed outward from the wrist band.

4. The method as in claim 1 wherein the optical portion of the PPG sensor is exposed through a face of a smart watch.

5. The method as in claim 1 wherein the one or more generalized transfer functions includes a first generalized transfer function that convert the average, inverted PPG signal to an un-calibrated, peripheral pressure waveform, and a second generalized transfer function to an un-calibrated, central pressure waveform.

6. The method as in claim 1 wherein one or more of the steps after the raw, analog PPG signal is converted to a digitized signal are implemented in the Cloud.

7. The method as in claim 1 wherein one or more of the steps after the raw, analog PPG signal is converted to a digitized signal are implemented on a smart phone.

8. The method as in claim 1 wherein the exposed optical portion of the PPG sensor is recessed relative to the surrounding surface of the PPG sensor, or is raised relative to the surrounding surface of the PPG sensor, such that a user's finger receives tactile feedback whether the entire optical portion has been covered by the user's finger.

9. A method of monitoring central blood pressure parameters comprising the steps of:
   providing a smart watch or smart band having a microcontroller unit (MCU) and a PPG sensor adapted to sense blood perfusion in the wrist of the person wearing the smart watch or smart band, said PPG sensor outputting a raw, analog PPG signal when the user places their lower wrist against an exposed optical portion of the PPG sensor;
   placing the user's lower wrist against the smart watch for a period of time sufficient to sense several blood pulse, and outputting a raw, analog PPG signal to the MCU;
   converting the raw, analog PPG signal to a digitized signal;
   processing the digitized signal through a low pass filter and a high pass filter;

inverting the digitized signal after it has been processed through the low pass and high pass filters;
detecting individual pulses in the digitized PPG signal after it has been filtered and inverted;
averaging several individual pulses to produce an average, un-calibrated PPG pulse;
applying one or more generalized transfer functions to the average, un-calibrated PPG pulse to generate an un-calibrated aortic pressure waveform with cardiovascular waveform features preserved, said preserved cardiovascular waveform features of the un-calibrated aortic pressure waveform comprising a first shoulder, a second shoulder and an incisura, said one or more generalized transfer functions representing a harmonic ratio in amplitude and phase to transform the average, un-calibrated PPG pulse to the un-calibrated aortic pressure waveform with cardiovascular waveform features preserved;
detecting waveform features in the un-calibrated aortic pressure waveform and calculating parameters pertaining to the un-calibrated aortic pressure waveform; and
displaying one or more of said calculated parameters or an indication of said calculated parameters.

10. The method as in claim 9 wherein the one or more generalized transfer functions includes a first generalized transfer function that convert the average, inverted PPG signal to an un-calibrated, peripheral pressure waveform, and a second generalized transfer function to an un-calibrated, central pressure waveform.

11. The method as in claim 9 wherein one or more of the steps after the raw, analog PPG signal is converted to a digitized signal are implemented in the Cloud.

12. The method as in claim 9 wherein one or more of the steps after the raw, analog PPG signal is converted to a digitized signal are implemented on a smart phone.

13. A method of monitoring central blood pressure parameters comprising the steps of:
providing a PPG sensor adapted to sense blood perfusion in the finger of a person, said PPG sensor outputting a raw, analog PPG signal when the person places their finger against an exposed optical portion of the PPG sensor;
placing the person's finger against the exposed optical portion of the PPG sensor for a period of time sufficient to sense several blood pulses, and outputting a raw, analog PPG signal to a microcontroller;
converting the raw, analog PPG signal to a digitized signal;
processing the digitized signal through a low pass filter and a high pass filter;
inverting the digitized signal after it has been processed through the low pass and high pass filters;
detecting individual pulses in the digitized PPG signal after it has been filtered and inverted;
averaging several individual pulses to produce an average, un-calibrated PPG pulse;
applying one or more generalized transfer functions to the average, un-calibrated PPG pulse to generate an un-calibrated aortic pressure waveform with cardiovascular waveform features preserved, said preserved cardiovascular waveform features of the un-calibrated aortic pressure waveform comprising a first shoulder, a second shoulder and an incisura, said one or more generalized transfer functions representing a harmonic ratio in amplitude and phase to transform the average, un-calibrated PPG pulse to the un-calibrated aortic pressure waveform with cardiovascular waveform features preserved;
detecting waveform features in the un-calibrated aortic pressure waveform and calculating parameters pertaining to the un-calibrated aortic pressure waveform; and
displaying one or more of said calculated parameters or an indication of said calculated parameters.

14. The method as in claim 13 wherein the PPG sensor is embedded in the housing of the smart watch or smart band and the optical portion of the PPG sensor is exposed through a side wall of the housing or through a bezel on the side wall of the housing.

15. The method as in claim 13 wherein the PPG sensor is attached to a wrist band configured to be worn by the person and the optical portion of the PPG sensor is exposed outward from the wrist band.

16. The method as in claim 13 wherein the PPG sensor is located on a laptop computer and the optical portion is exposed so the person is able to place their index finger over the optical portion of the PPG sensor to take blood perfusion measurements in the person's finger.

17. The method as in claim 13 wherein the PPG sensor is located on one of the buttons of a computer mouse and the optical portion is exposed so the person is able to place their index finger over the optical portion of the PPG sensor to take blood perfusion measurements in the person's finger.

18. The method as in claim 13 wherein the one or more transfer functions includes a first generalized transfer function that convert the average, inverted PPG signal to an un-calibrated, peripheral pressure waveform, and a second generalized transfer function to an un-calibrated, central pressure waveform.

19. The method as in claim 13 wherein one or more of the steps after the raw, analog PPG signal is converted to a digitized signal are implemented in the Cloud.

20. The method as in claim 13 wherein the exposed optical portion of the PPG sensor is recessed relative to the surrounding surface of the PPG sensor, or is raised relative to the surrounding surface of the PPG sensor, such that the person's finger receives tactile feedback whether the entire optical portion has been covered by the person's finger.

* * * * *